United States Patent [19]

Ohkawara et al.

[11] Patent Number: 5,506,188
[45] Date of Patent: Apr. 9, 1996

[54] ADSORPTIVE MATERIALS AND PROCESS FOR PRODUCING THEM

[75] Inventors: Tadayoshi Ohkawara, Gunma; Kyoichi Saito, Tokyo; Etsuko Sugo, Gunma, all of Japan

[73] Assignee: Angel Research Institute Co., Japan

[21] Appl. No.: 217,050

[22] Filed: Mar. 24, 1994

[30] Foreign Application Priority Data

Mar. 25, 1993 [JP] Japan .................................. 5-066397
Dec. 28, 1993 [JP] Japan .................................. 5-355133

[51] Int. Cl.$^6$ ............................ B01J 20/26; B01J 21/04; B01J 23/02
[52] U.S. Cl. ........................................ 502/402; 502/439
[58] Field of Search ................................ 502/402, 439

[56] References Cited

U.S. PATENT DOCUMENTS 4,076,619  2/1978  Howery .

FOREIGN PATENT DOCUMENTS 0337144    3/1989   European Pat. Off. .
0486015A1  11/1991  European Pat. Off. .
0503651A1   3/1992  European Pat. Off. .
1-257418   10/1989  Japan .
2-69123     3/1990  Japan .
1230363     4/1971  United Kingdom .
WO92/00805  7/1991  WIPO .

OTHER PUBLICATIONS

EP Search Report of Application No. 94104743.3.
Sugo, "The Synthesis of a New Type Adsorbent for the Removal of Toxic Gas/Characteristics and Application", *JPI Journal*, 28(5):532–540 (1990) (English Abstract).

*Primary Examiner*—Sharon Gibson
*Attorney, Agent, or Firm*—Banner & Allegretti

[57] ABSTRACT

The specification relates to an adsorptive material for removing malodorous substances from gases and liquids. The adsorptive material comprises a substrate having macromonomers which are bonded to the substrate and contain functional groups capable of adsorbing polar substances. The adsorptive material is produced by applying to the substrate a mixture of a monosaccharide and the macromonomers and then grafting the macromonomers to the substrate.

29 Claims, No Drawings

ADSORPTIVE MATERIALS AND PROCESS FOR PRODUCING THEM

BACKGROUND OF THE INVENTION

This invention relates to adsorptive materials for removing malodorous substances from gases and liquids, as well as a process for producing such adsorptive materials. More particularly, this invention relates to adsorptive materials for removing malodorous substances in such items as clothes, bedclothes, pillow covers as well as animal laboratories, residences, hospitals and automobiles and to a process for producing such adsorptive materials.

With recent improvements in living standards, not only the malodor from industrial plants but also malodor originating from various sources in everyday life such as toilets, garbage, sewage and pet animals have become a social concern. The causative substances of malodor include, for example, ammonia, amines, hydrogen sulfide and mercaptans. Various methods are available for removing malodors originating from everyday life and they include, for example: spraying or evaporating fragrance substances; cleaning with chemicals such as acids or alkalies; adsorbing malodorous substances on zeolite or bentonite; using catalysts or oxidizers; and neutralizing malodorous substances with ion exchangers.

Japanese Patent Public Disclosure (KOKAI) No. Hei 2-69123 teaches a chemical for clearing excretions from pet animals. The chemical comprises a water-absorbing polymeric powder that is incorporated in a powder comprising a nonmetallic mineral having ion-exchange capability and adsorptive power.

Japanese Patent Publication (KOKOKU) No. Hei 8-8738 teaches a dry particulate material for treating excretions from domesticated animals and contains chemical pulp, mechanical pulp or semichemical pulp and an inorganic filler.

U.S. Pat. No. 4,076,619 to Howery teaches a crosslinked acrylic polymer capable of selective adsorption of waste matter as excreted by fish and shellfish in seawater.

However, these conventional methods have been unable to yield completely satisfactory results since their ability to remove malodorous substances is either insufficient or limited to particular substances.

SUMMARY OF THE INVENTION

The present invention has been accomplished under these circumstances and has as an object of providing an adsorptive material that is capable of adsorbing a wide spectrum of malodorous substances with improved efficiency.

This object of the present invention can be attained by an adsorptive material comprising a substrate having macromonomers, the macromonomers being bonded to the substrate and containing functional groups capable of adsorbing polar substances.

DESCRIPTION OF THE PREFERRED EMBODIMENT

The substrate of the adsorptive material of the present invention is not limited to any particular type, and any materials that permit the binding of the macromonomer can be used. Substrates that can be used in the present invention include, for example, celluloses, polyolefins, polyacrylonitriles, polyesters such as PET and PBT, polyamides such as nylon 6 and nylon 66, animal hairs, natural leather and synthetic leather, as well as combinations of these.

Typical examples of the celluloses that can be used as the substrate include wood celluloses such as paper pulp and wood chips. In addition to these celluloses, leaf fiber cellulose, stem fiber cellulose and seed tomentous or pubescent fiber cellulose may also be used. Examples of such celluloses include bast fibers (e.g., hemp, flax, ramie and Manila hemp) and cotton. If desired, rice straw, coffee bean husk, spent tea leaves, soy pulp and other waste may be recycled for use as cellulose. Such waste is very convenient to use as substrates because it does not require any special preliminary treatments. A particularly preferred cellulose for use in the present invention is paper pulp.

Examples of polyolefins that can be used as a substrate include polyethylene and polypropylene. If desired, these materials may be partly replaced by halogens such as chlorine and fluorine, hydroxyl group, etc. A preferred polyolefin is polyethylene.

Examples of animal hairs that can be used as substrates include wool, camel hair, alpaca, cashmere, mohair, goat hair, rabbit hair and silk.

Examples of natural leather that can be used as substrates include cowskin, goatskin and the skin or hide of reptiles.

Examples of synthetic leather that can be used as substrates include CORFAM (registered trademark) of Du Pont, CLARINO (registered trademark) of Kuraray and ECSAINE (registered trademark) of Toray.

The substrate of the adsorptive material of the present invention has the function of serving as a structural member that supports the macromonomers having functional groups capable of adsorbing polar substances, increases the area of adsorption, retains the shape of the adsorptive material and imparts the necessary strength. Hence, the substrate itself is generally a material that is essentially nonreactive, or inert, to polar substances. On the other hand, polar substances are to be adsorbed by the macromonomers to be described hereinafter. Thus, one of the major features of the present invention is that the substrate and the macromonomers respectively assume two different parts of the function of the adsorptive material. As a result, the adsorptive material of the present invention has an increased area of adsorption while exhibiting physical and chemical stability. Unlike the adsorptive material of the present invention, conventional ion-exchange resins do not rely upon the substrate and functional groups to perform different functions since they have been produced by a process in which a polymerizable monomer having ion-exchange groups is polymerized to form a high-molecular material.

The shape of the substrate is not limited in any particular way and various shapes may be employed as selected from among fibers, films, flakes, powders, sheets, mats and spheres. From the viewpoint of maximizing the area of adsorption and enhancing the efficiency of adsorption, the use of fibrous materials is advantageous. It is particularly advantageous to use fibrous materials having fiber diameters of from about 1 to about 50 μm. One of the reasons why fibrous materials are advantageous is that they can be easily worked into a desired shape and assembled in a module. Further, fibrous materials have no potential to release fine particles or dust into the atmosphere and, hence, they can be used in semiconductors and other areas of precision machining. If fibrous materials are to be used, they may be staple fibers or filaments. Such fibers may be processed into woven or nonwoven fabrics. If fibrous materials are to be used in a spherical form, their diameter is advantageously adjusted to lie between about 2 and 20 mm from the viewpoint of ease of handling. It should also be mentioned that if the adsorptive material of the present invention employs a fibrous substrate, it may be used in admixture with other fibrous materials.

The macromonomers that are bonded to the substrate of the adsorptive material of the present invention and which have functional groups capable of adsorbing polar substances comprise the product of polymerization of reactive monomers described below. The term "macromonomer" as used herein means a polymerized material having a degree of polymerization intermediate between the values for an oligomer and a higher polymer. The macromonomers to be used in the present invention preferably have a degree of polymerization in the range from about 10 to about 100, with the range from about 50 to about 100 being more preferred. Thus, the macromonomers to be used in the present invention are the polymerized material of reactive monomers having functional groups capable of adsorbing polar substances and have a degree of polymerization of from about 10 to about 100. As will be described later in this specification, the adsorptive material of the present invention is produced by grafting to the substrate the macromonomers which have functional groups capable of adsorbing polar substances. Therefore, the adsorptive material of the present invention and a graft polymer that is produced by graft polymerization of reactive monomers onto a substrate are distinguished from each other in terms of both chemical structure and production process.

Functional groups to be used in the present invention that have the ability to adsorb polar substances include, for example hydrophilic groups, cationically dissociating groups and anionically dissociating groups. Preferably, the functional groups comprise hydrophilic groups and cationically dissociating groups and/or anionically dissociating groups. Stated more specifically, the macromonomer contains preferably either two kinds of functional groups (i.e., hydrophilic groups and cationically dissociating groups, or hydrophilic groups and anionically dissociating groups) or three kinds of functional groups (i.e., hydrophilic groups, cationically dissociating groups and anionically dissociating groups). Thus, one of the major features of the adsorptive material of the present invention is that hydrophilic groups (nonions) are present in combination with ionic groups (cations and/or anions).

Hydrophilic groups, cationically dissociating groups and anionically dissociating groups are introduced into the macromonomer by insuring that reactive monomers having these groups (to be described below) are polymerized to a degree of polymerization within the range specified above (i.e., ca. 10 –ca. 100). Stated more specifically, the macromonomer can generally be prepared by polymerizing a solution containing a mixture of reactive monomers that have the functional groups described above. Various methods of polymerization may be employed, such as polymerization in the presence of a polymerization initiator, thermal polymerization and ionizing radiation initiated polymerization. In these cases, the desired degree of polymerization can be attained by controlling the reaction conditions in an appropriate manner. In the case of ionizing radiation initiated polymerization, ultraviolet rays, electron beams, X-rays, $\alpha$-rays, $\beta$-rays, $\gamma$-rays, etc. may be used. Thus, the resulting macromonomer comprises reactive monomers having hydrophilic groups and reactive monomers having cationically dissociating groups and/or reactive monomers having anionically dissociating groups. When preparing the macromonomer, the molar ratio at which the reactive monomers having hydrophilic groups, the reactive monomers having cationically dissociating groups and the reactive monomers having anionically dissociating groups are to be mixed can be selected as appropriate for such factors as the use and performance of the adsorptive material to be finally produced. To give just one example, a solution comprising a mixture of about 5 to about 20 mol % of the reactive monomers having hydrophilic groups, about 30 to about 50 mol % of the reactive monomers having cationically dissociating groups, and about 30 to about 50 mol % of the reactive monomers having anionically dissociating groups may be polymerized to produce the macromonomer.

There is no particular limitation on the mode in which the reactive monomers having hydrophilic groups and the reactive monomers having cationically and/or anionically dissociating groups are arranged in the macromonomer. Therefore, the reactive monomers having hydrophilic groups and the reactive monomers having cationically and/or anionically dissociating groups may be arranged alternately, in blocks, randomly or in grafts. The mode of arrangement of these reactive monomers depends on the reaction conditions or the type of reactive monomers to be used when producing the macromonomer and appropriate reaction conditions can be selected by anyone skilled in the art.

The term "hydrophilic groups" as used herein means those groups which have affinity for water and which will not dissociate ionically upon contact with water; in other words, hydrophilic groups are nonions. Such hydrophilic groups are capable of trapping the water molecules present in air and the trapped water molecules are capable of forming a layer of adsorbed water on the surface of the adsorptive material of the present invention, thereby dissolving polar substances and/or dissociating ionic substances. Needless to say, such hydrophilic groups will function in water in the same manner as in air.

Examples of such hydrophilic groups include a hydroxyl group, a hydroxyalkyl group (where the alkyl group is preferably a lower alkyl group), an amino group and a pyrrolidonyl group. Preferred hydrophilic groups include a hydroxyl group, a hydroxyalkyl group and a pyrrolidonyl group. One or more kinds of hydrophilic groups may be introduced into the macromonomer. Reactive monomers that have such hydrophilic groups and which are useful in the present invention include, for example, hydroxyethyl methacrylate, hydroxypropyl acrylate, vinylpyrrolidone, dimethylacrylamide, ethylene glycol monomethacrylate, ethylene glycol monoacrylate, ethylene glycol dimethacrylate, ethylene glycol diacrylate, triethylene glycol diacrylate and triethylene glycol methacrylate. Among these, hydroxyethyl methacrylate and vinylpyrrolidone are particularly useful hydrophilic monomers.

The term "cationically dissociating groups" as used herein means those ion-exchange groups whose counter ion is a cation. A typical cationically dissociating group is an acid group. Catlonlcally dissociating groups have the ability to adsorb polar substances and are capable of releasing a proton (hydrogen ion) to enter into neutralizing reaction with basic substances, say, ammonia or amines. As a result, the basic substances will be removed. One or more kinds of cationically dissociating groups may be introduced into the macromonomer.

Examples of such cationically dissociating groups include a carboxyl group, a sulfone group, a phosphate group, a sulfoethyl group, a phosphomethyl group, a carbomethyl group. Preferred cationically dissociating groups include a sulfone group and a carboxyl group. Reactive monomers that have such cationically dissociating groups and which are useful in the present invention include, for example, acrylic acid, methacrylic acid, styrenesulfonic acid and salts thereof, and 2-acrylamido-2-methylpropanesulfonic acid. Also useful in the present invention are reactive monomers that have groups capable of conversion to cationically dissociating groups. Examples of such reactive monomers include glycidyl methacrylate and glycidyl acrylate.

The term "anionically dissociating groups" as used herein means those ion-exchange groups whose counter ion is an anion. Therefore, anionically dissociating groups have the ability to absorb polar substances and are capable of entering into neutralizing reaction with acidic substances, say, hydrogen sulfide or mercaptans. As a result, the acidic substances will be removed. One or more kinds of anionically dissociating substances may be introduced into the macromonomer.

Examples of such anionically dissociating groups include a quaternary ammonium salt and primary, secondary and tertiary aminos groups such as an amino group, a methylamino group, a dimethylamino group and a diethylamino group. Preferred anionically dissociating groups include a quaternary ammonium salt and an amino group. Reactive monomers that have such anionically dissociating groups and which are useful in the present invention include, for example, vinylbenzyltrimethyl ammonium salt, diethylaminoethyl methacrylate, dimethylaminoethyl acrylate, dimethylaminoethyl methacrylate, diethylaminoethyl acrylate, diethylaminomethyl methacrylate, tertiary-butylaminoethyl acrylate, tertiary-butylaminoethyl methacrylate and dimethylaminopropylacrylamide. Among these, vinylbenzyltrimethyl ammonium salt and diethylaminoethyl methacrylate are particularly useful. Also useful in the present invention are reactive monomers that have groups capable of conversion to anionically dissociating groups. An example of such a reactive monomer is chloromethylstyrene.

In the present invention, one or more kinds of hydrophilic groups may be present in the macromonomer. This is also true with cationically dissociating groups and anionically dissociating groups and one or more kinds of each group may be present in the macromonomer.

Combinations of functional groups that are preferred in the present invention may specifically be exemplified by the one of a sulfone group with a carboxyl group, a quaternary ammonium group and a hydroxyethyl group. Another specific preferred example of the combination of functional groups is the one of a sulfone group with a carboxyl group, a quaternary ammonium salt and a pyrrolidonyl group.

Needless to say, the thus prepared macromonomer which has functional groups capable of adsorbing polar substances may be used as such without being bonded to the substrate. Thus, the macromonomer may be diluted and charged into a spray can for subsequent use as an aerosol-type deodorizing spray. However, in the present invention, the macromonomer is bonded to the substrate considering the fact that the use of the adsorptive material is expanded by immobilizing the macromonomer on the substrate of an existing shape in a manner that is stable both physically and chemically.

In the adsorptive material of the present invention, the macromonomer is bonded chemically to the substrate. While any known binding methods may be employed, graft polymerization techniques to be described below, in particular, radiation initiated graft polymerization that uses monosaccharides is preferably employed.

The adsorptive material of the present invention performs adsorption by the following mechanism. The adsorptive material comprises the substrate for retaining its shape and imparting the necessary strength, as well as the macromonomer which binds to said substrate. The macromonomer contains functional groups having the ability to adsorb polar substances, in particular, hydrophilic groups and cationically dissociating groups and/or anionically dissociating groups. Consider here the case of adsorption in air; the water molecules that are present in air are attracted towards the surface of the adsorptive material by means of hydrophilic groups and then adsorbed on that surface. Thus, the layer of adsorbed water comprising a number of adsorbed water molecules is formed on the surface of the adsorptive material. Acidic or basic substances will be trapped on the surface of the adsorptive material by interaction with the cationically or anionically dissociating groups while, at the same time, they are also trapped on the surface of the adsorptive material by the action of adsorbed water. The thus trapped substances will dissociate in the layer of adsorbed water to be neutralized with cationically or anionically dissociating groups. As For ordinary polar substances, their affinity for water causes them to be dissolved in the layer of adsorbed water. Thus, the presence of hydrophilic groups and cationically and/or anionically dissociating groups in the adsorptive material of the present invention enhances not only the adsorbability of target substances but also their tendency for dissociation. In short, the adsorptive material of the present invention is in such a state that adsorption, dissociation and reaction for neutralization are most likely to occur, causing two kinds of adsorption, one being physical adsorption that involves dissolution in water and the other being chemical adsorption which involves dissociation into ions and neutralization.

The substances to be adsorbed on the adsorptive material of the present invention by the mechanism described above may be of any types as long as they are polar substances. Preferably, they are acidic substances such as mercaptan and hydrogen sulfide, or basic substances such as ammonia and amine containing substances.

While the mechanism of adsorption by the adsorptive material of the present invention has been described above with reference to the case where adsorption occur in air, it will be apparent to one skilled in the art that the same mechanism will apply to adsorption that occurs in water.

As described above, the adsorptive material of the present invention permits efficient removal of various polar substances and, hence, it can be used in a broad scope of applications including padding for suits, feed materials for animals, air conditioning filters, articles for use in hospitals (e.g., pillows and bed sheets), filters in automotive air conditioners, refrigerators, in soles for shoes, disposable diapers and fast food kitchens.

In addition to the above-described adsorptive material, the present invention also provides a process for producing said adsorptive material. Stated more specifically, the present invention also provides a process for producing an adsorptive material comprising the steps of applying to a substrate a mixture of a monosaccharide and macromonomers having functional groups capable of adsorbing polar substances and then grafting said macromonomers to said substrate.

In the current practice of grafting macromonomers to substrates, the low affinity between the surfaces of the two members prevents effective grafting of the macromonomers to the substrate and, instead, the macromonomers undergo homopolymerization which will proceed independently of the intended graft polymerization. Hence, it has been very difficult to graft the macromonomers onto the surface of the substrate. The process of the present invention eliminates these defects of the prior art and renders it possible to have the macromonomers grafted efficiently onto the substrate.

To implement the process of the present invention, the substrate already described in connection with the first aspect of the invention is formed into a desired shape, say, a woven cloth of fibers and, thereafter, a mixture of the macromonomers and a monosaccharide is applied to the shaped substrate. The macromonomers are such that they have been prepared by the method already described in connection with the first aspect of the invention. The method of applying the mixture of the macromonomers and the monosaccharide to the substrate is in no way limited and various means of application can be employed as exemplified by coating with a brush or a doctor blade, spraying, and impregnation. The proportions at which the macromonomers and the monosaccharide are to be mixed are by no means critical for the purposes of the present invention and they can be determined appropriately by one skilled in the art in such a way as to provide a desired graft ratio. For example, the monosaccharide is added generally in an amount of from about 0.1 to about 10 wt %, preferably from about 0.5 to about 5 wt %, more preferably from about 1 to about 3 wt %, on the basis of the total weight of the macromonomers. If the substrate is fibrous, the fiber diameter is preferably from about 1 to about 50 μm because this range insures graft polymerization to take place uniformly in fiber cross sections.

After the substrate is impregnated with the mixture of the macromonomers and the monosaccharide, the excess portion of the mixture is removed from the substrate and the remaining portion is subjected to graft polymerization. There is no particular limitation on the method of graft polymerization and various techniques can be employed, including polymerization in the presence of a polymerization initiator, thermal polymerization in the presence of a reaction initiator, thermal polymerization and ionizing radiation initiated polymerization. Graft polymerization to be initiated by exposure to ionizing radiations is preferably employed in the present invention. Examples of the ionizing radiation that can be used include ultraviolet rays, electron beams, X-rays, α-rays, β-rays, γ-rays, etc. For practical applications, γ-rays or electron beams are preferably used. The graft ratio is in no way limited in the present invention but it is preferably no more than about 150%, with the range from about 50 to about 100% being particularly preferred. If the graft ratio is excessive, the inherent properties of the substrate will be impaired to increase the chance of its failure to perform the intended functions already described above.

One of the major features of the process of the present invention is to use monosaccharides in graft polymerization. The purpose of using monosaccharides is to achieve a marked improvement in the efficiency of grafting the macromonomers onto the substrate. The use of monosaccharide improves the graft ratio probably because they accelerate the impregnation of the macromonomers into the substrate. As a result, chemical bonds will be easily formed between the macromonomers and the substrate by graft polymerization, accompanied by corresponding decrease in the homopolymerization between molecules of the macromonomers. Therefore, it is believed that monosaccharides will participate in the formation of chemical bonds between the macromonomers and the substrate but they would not probably be part of the formed chemical bonds.

The monosaccharides to be used in the process of the present invention are aldoses or ketoses represented by the general formula $C_nH_{2n}O_n$, where n is an integer of 2–10. Aldoses are preferably used in the present invention and it is particularly preferred to use glucose which is aldohexose (n=6).

The adsorptive material of the present invention contains not only hydrophilic groups but also cationically dissociating groups and/or anionically dissociating groups; hence, said material is capable of adsorbing acidic or basic substances while achieving simultaneous adsorption of ordinary polar substances. What is more, the efficiency of their adsorption is extremely high. When implementing the process of the present invention for producing the adsorptive material, the efficiency of grafting the macromonomers onto the substrate can be enhanced markedly by using monosaccharides.

The following examples are provided for the purpose of further illustrating the present invention but are in no way to be taken as limiting.

EXAMPLE 1

A glass container was charged with 1 L of an aqueous solution containing a mixture of sodium styrenesulfonate (100 g), acrylic acid (100 g) and vinylpyrrolidone (10 g). High-purity nitrogen was bubbled through the aqueous solution for 1 min to replace the dissolved oxygen. Subsequently, the aqueous solution was irradiated with a uv radiation (200 W) at 40° C. for 1 h, thereby effecting polymerization to prepare a macromonomer. The degree of polymerization of the macromonomer was about 80. Glucose (10 g) was added to the resulting macromonomer solution and dissolved thoroughly to prepare a solution comprising a mixture of the macromonomer and glucose.

Flakes of regenerated paper having an average diameter of 5 mm were immersed in an equal volume of the mixture solution for 10 min. Subsequently, the regenerated paper was recovered from the mixture solution, stripped of excess residual liquid and charged into an irradiation vessel. After deoxygenating the interior of the vessel, the regenerated paper was irradiated with γ-rays from cobalt 60 at a dose rate of 10 kGy/h for 2 h at room temperature, whereby the macromonomer was grafted onto the regenerated paper to produce a sample of the invention's adsorptive material. The absorbed dose was 20 kGy. The sample was washed thoroughly with warm water to remove the unreacted macromonomer and the homopolymer of the macromonomer. Thus, an adsorptive material was obtained such that the macromonomer containing pyrrolidonyl, carboxyl and sulfone groups was bonded thereto. After drying, the change in the weight of the adsorptive material was measured and the graft ratio was found to be 95 wt % of the impregnant macromonomer. The adsorptive material had no detectable deposit of a homopolymer of the macromonomer. Measurement of ion-exchange capacity showed that 4.0 mmol of cation-exchange groups had been introduced per gram of the adsorptive material.

The thus produced adsorptive material was then tested for its adsorbing performance. A portion (20 g) of the adsorptive material was placed in the central square part (10 cm per side) of the bottom of a polyacrylic container having a capacity of 150 L. Ammonia was supplied into the container to give an initial concentration of 100 ppm. The concentration of ammonia in the container was measured with a GASTEC detector at predetermined time intervals. The measurement was continued until the concentration of ammonia in the container dropped from 100 ppm to 20 ppm. When the ammonia concentration reached 20 ppm, ammonia was supplied again into the container to give a concentration of 100 ppm, followed by another measurement until the concentration dropped to 20 ppm. This operation was repeated and the point of time at which the concentration of ammonia would no longer reach 20 ppm after passage of 5 h was regarded as "breakthrough". The adsorption capacity of the adsorptive material was calculated from the integration of the amount of ammonia that had been adsorbed until breakthrough was reached and the result was 3.5 mmol/g. For comparison, a commercial grade of deodorizing activated charcoal was measured for its adsorption capacity by the same method and the result was 0.03 mmol/g. It is therefore clear that the adsorptive material of the present invention had an extremely large adsorption capacity.

Comparative Example 1

A macromonomer was prepared by the same procedure as in Example 1. Then, the macromonomer was grafted onto regenerated paper by the same procedure as in Example 1, except that no glucose was used. The resulting adsorptive material had a homopolymer of the macromonomer formed on the surface of the regenerated paper and the homopolymer came off the substrate upon washing with warm water. The dried adsorptive material was brittle. The change in the weight of the adsorptive material was measured and the graft ratio was found to be 30% of the impregnant macromonomer. Measurement of ion-exchange capacity showed that 0.7 mmol of cation-exchange groups had been introduced per gram of the adsorptive material.

In the next place, the thus produced adsorptive material was tested for its adsorbing performance by the same procedure as in Example 1. The adsorption capacity of the adsorptive material was found to be 0.3 mmol/g.

Thus, it was clear that when the macromonomer was grafted onto the substrate without using the monosaccharide glucose, not only the efficiency of polymerization but also the adsorption capacity of the resulting adsorptive material was low.

Comparative Example 2

In this comparative example, reactive monomers were directly grafted to the substrate without preparing a macromonomer.

Regenerated paper was impregnated in an aqueous mixture solution for macromonomer preparation as used in Example 1, and graft polymerization was conducted by the same method as in Example 1. As a result, the aqueous mixture solution moved to the bottom of the irradiation vessel, producing homopolymers in blocks. The graft ratio was 40% of the impregnant reactive monomers. Measurement of ion-exchange capacity showed that 1.2 mmol of cation-exchange capacity showed that 1.2 mmol of cation-exchange groups had been introduced per gram of the adsorptive material.

In the next place, the thus produced adsorptive material was tested for its adsorbing performance by the same procedure as in Example 1. The adsorption capacity of the adsorptive material was found to be 1.0 mmol/g.

Thus, it was clear that when reactive monomers were directly grafted onto the substrate without preparing a macromonomer, not only the efficiency of polymerization but also the adsorption capacity of the resulting adsorptive material was low.

EXAMPLE 2

A glass container was charged with 1 L of an aqueous solution containing a mixture of diethylaminoethyl methacrylate (300 g) and hydroxyethyl methacrylate (50 g). High-purity nitrogen was bubbled through the aqueous solution for 1 min to replace the dissolved oxygen. Subsequently, the aqueous solution was irradiated with γ-rays from cobalt 60 at a dose rate of 0.1 kGy/h for 1 h at room temperature to prepare a macromonomer. The degree of polymerization of the macromonomer was about 85. Glucose (10 g) was added to the resulting macromonomer solution and dissolved thoroughly to prepare a solution comprising a mixture of the macromonomer and glucose.

A polyethylene filter cloth having a fiber diameter of 25 μm was immersed in an equal volume of the mixture solution for 10 min. Subsequently, the filter cloth was recovered from the mixture solution, stripped off excess residual liquid and charged into an irradiation vessel. After deoxygenating the interior of the vessel, the filter cloth was irradiated with γ-rays from cobalt 60 at a dose rate of 10 kGy/h for 2 h at room temperature, whereby the macromonomer was grafted onto the filter cloth to produce a sample of the invention's adsorptive material. The adsorbed dose was 20 kGy. The sample was washed thoroughly with warm water to remove the unreacted macromonomer and the homopolymer of the macromonomer. Thus, an adsorptive material was obtained such that the macromonomer containing hydroxyethyl and diethylamino groups was bonded thereto. After drying, the change in the weight of the adsorptive material was measured and the draft ratio was found to be 98 wt % of the impregnant macromonomer. The adsorptive material had no detectable deposit of a homopolymer of the macromonomer. Measurement of ion-exchange capacity showed that 3.5 mmol of anion-exchange groups had been introduced per gram of the adsorptive material.

In the next place, the thus produced adsorptive material was tested for its adsorbing performance by the same procedure as in Example 1, except that acetic acid was used instead of ammonia. The adsorptive material was found to have an adsorption capacity of 3.5 mmol/g. For comparison, a commercial grade of deodorizing activated charcoal was measured for its adsorption capacity by the same method and the result was 0.01 mmol/g. It is therefore clear that the adsorptive material of the present invention had an extremely large adsorption capacity.

Comparative Example 3

A macromonomer was prepared by the same procedure as in Example 2. Then, the macromonomer was grafted onto a polyethylene filter cloth by the same procedure as in Example 2, except that no glucose was used. The resulting adsorptive material had a homopolymer of the macromonomer formed on the surface of the filter cloth and the homopolymer came off the substrate upon washing with warm water. The change in the weight of the adsorptive material was measured and the graft ratio was found to be 45% of the impregnant macromonomer. Measurement of ion-exchange capacity showed that 1.3 mmol of anion-exchange groups had been introduced per gram of the adsorptive material.

In the next place, the thus produced adsorptive material was tested for its adsorbing performance by the same procedure as in Example 2. The adsorption capacity of the adsorptive material was found to be 1.0 mmol/g.

Thus, it was clear that when the macromonomer was grafted onto the substrate without using the monosaccharide glucose, not only the efficiency of polymerization but also the adsorption capacity of the resulting adsorptive material was low.

Comparative Example 4

In this comparative example, reactive monomers were directly grafted to the substrate without preparing a macromonomer.

Polyethylene filter cloth was impregnated in an aqueous mixture solution for macromonomer preparation as used in Example 2, and graft polymerization was conducted by the same method as in Example 2. As a result, the aqueous mixture solution moved to the bottom of the irradiation vessel, producing homopolymers in blocks. The graft ratio was 20% of the impregnant reactive monomers. Measurement of ion-exchange capacity showed that 0.6 mmol of cation-exchange groups had been introduced per gram of the adsorptive material.

In the next place, the thus produced adsorptive material was tested for its adsorbing performance by the same procedure as in Example 1. The adsorption capacity of the adsorptive material was found to be 0.5 mmol/g.

Thus, it was clear that when reactive monomers were directly grafted onto the substrate without preparing a macromonomer, not only the efficiency of polymerization but also the adsorption capacity of the resulting adsorptive material was low.

EXAMPLE 3

A glass container was charged with 1 L of an aqueous solution containing a mixture of dimethylaminoethyl acrylate (300 g) and vinylpyrrolidone (100 g). High-purity nitrogen was bubbled through the aqueous solution for 1 min to replace the dissolved oxygen. Subsequently, the aqueous solution was irradiated with γ-rays from cobalt 60 at a dose rate of 0.5 kGy/h for 1 h at room temperature to prepare a macromonomer. The degree of polymerization of the macromonomer was about 90. Glucose was added to the resulting macromonomer solution in an amount of 1% of the total quantity of the macromonomer and dissolved thoroughly to prepare a solution comprising a mixture of the macromonomer and glucose.

A nonwoven polyethylene terephthalate fabric having a fiber diameter of 30 μm was immersed in an equal volume of the mixture solution for 10 min. Subsequently, the nonwoven fabric was recovered from the mixture solution, striped off excess residual liquid and charged into an irradiation vessel. After deoxygenating the interior of the vessel, the nonwoven fabric was irradiated with γ-rays from cobalt 60 at a dose rate of 10 kGy/h for 2 h at room temperature, whereby the macromonomer was grafted onto the nonwoven fabric to produce a sample of the invention's adsorptive material. The sample was washed thoroughly with warm water to remove the unreacted macromonomer and the homopolymer of the macromonomer. Thus, an adsorptive material was obtained such that the macromonomer containing pyrrolidonyl and dimethylamino groups was bonded thereto. After drying, the change in the weight of the adsorptive material was measured and the graft ratio was found to be 95 wt % of the impregnant macromonomer. The adsorptive material had no detectable deposit on a homopolymer of the macromonomer. Measurement of ion-exchange capacity showed that 3.0 mmol of anion-exchange groups had been introduced per gram of the adsorptive material.

EXAMPLE 4

A glass container was charged with 1 L of an aqueous solution containing a mixture of dimethylaminoethyl methacrylate (300 g) and triethylene glycol diacrylate (100 g). High-purity nitrogen was bubbled through the aqueous solution for 1 min to replace the dissolved oxygen. Subsequently, the aqueous solution was irradiated with γ-rays from cobalt 60 at a dose rate of 1.0 kGy/h for 1 h at room temperature to prepare a macromonomer. The degree of polymerization of the macromonomer was about 100. Glucose was added to the resulting macromonomer solution in an amount of 5% of the total quantity of the macromonomer and dissolved thoroughly to prepare a solution comprising a mixture of the macromonomer and glucose.

A nonwoven nylon 66 fabric having a fiber diameter of 25 μm was immersed in an equal volume of the mixture solution for 10 min. Subsequently, the nonwoven fabric was recovered from the mixture solution, stripped of excess residual liquid and charged into an irradiation vessel. After deoxygenating the interior of the vessel, the nonwoven fabric was irradiated with γ-rays from cobalt 60 at a dose rate of 10 kGy/h for 2.5 h at room temperature, whereby the macromonomer was grafted onto the nonwoven fabric to produce a sample of the invention's adsorptive material. The sample was washed thoroughly with warm water to remove the unreacted macromonomer and the homopolymer of the macromonomer. After drying, the change in the weight of the adsorptive material was measured and the graft ratio was found to be 90 wt % of the impregnant macromonomer. The adsorptive material had no detectable deposit of a homopolymer of the macromonomer. Measurement of ion-exchange capacity showed that 2.0 mmol of anion-exchange groups had been introduced per gram of the adsorptive material.

EXAMPLE 5

A glass container was charged with 1 L of an aqueous solution containing a mixture of sodium styrenesulfonate (150 g), acrylic acid (150 g) and hydroxyethyl methacrylate (150 g). High-purity nitrogen was bubbled through the aqueous solution for 1 min to replace the dissolved oxygen. Subsequently, the aqueous solution was irradiated with γ-rays from cobalt 60 at a dose rate of 0.1 kGy/h for 1 h at room temperature to prepare a macromonomer. The degree of polymerization of the macromonomer was about 80. Glucose was added to the resulting macromonomer solution in an amount of 2% the total quantity of the macromonomer and dissolved thoroughly to prepare a solution comprising a mixture of the macromonomer and glucose.

Scoured wool yarns were immersed in an equal volume of the mixture solution for 1 min. Subsequently, the yarns was recovered from the mixture solution, stripped off excess residual liquid and charged into an irradiation vessel. After deoxygenating the interior of the vessel, the yarns were irradiated with γ-rays from cobalt 60 at a dose rate of 10 kGy/h for 2 h at room temperature, whereby the macromonomer was grafted onto the yarns to produce a sample of the invention's adsorptive material. The sample was washed thoroughly with warm water to remove the unreacted macromonomer and the homopolymer of the macromonomer. After drying, the change in the weight of the adsorptive material was measured and the graft ratio was found to be 98 wt % of the impregnant macromonomer. The adsorptive material had no detectable deposit of a homopolymer of the macromonomer. Measurement of ion-exchange capacity showed that 4.5 mmol of cation-exchange groups had been introduced per gram of the adsorptive material.

EXAMPLE 6

A glass container was charged with 1 L of an aqueous solution containing a mixture of dimethylaminopropyl acrylamide (300 g) and ethylene glycol dimethacrylate (100 g). High-purity nitrogen was bubbled through the aqueous solution for 1 min to replace the dissolved oxygen. Subsequently, the aqueous solution was irradiated with γ-rays from cobalt 60 at a dose rate of 0.1 kGy/h for 1 h at room temperature to prepare a macromonomer. The degree of polymerization of the macromonomer was about 90. Glucose was added to the resulting macromonomer solution in an amount of 3% of the total quantity of the macromonomer and dissolved thoroughly to prepare a solution comprising a mixture of the macromonomer and glucose.

Sheep skin was immersed in an equal volume of the mixture solution for 10 min. Subsequently, the sheep skin was recovered from the mixture solution, stripped of excess residual liquid and charged into an irradiation vessel. After deoxygenating the interior of the vessel, the sheep skin was irradiated with γ-rays from cobalt 60 at a dose rate of 10 kGy/h for 2.5 h at room temperature, whereby the macromonomer was grafted onto the sheep skin to produce a sample of the invention's adsorptive material. The sample was washed thoroughly with warm water to remove the unreacted macromonomer and the homopolymer of the macromonomer. After drying, the change in the weight of the adsorptive material was measured and the graft ratio was found to be 93 wt % of the impregnant macromonomer. The adsorptive material had no detectable deposit of a homopolymer of the macromonomer. Measurement of ion-exchange capacity showed that 3.0 mmol of anion-exchange groups had been introduced per gram of the adsorptive material.

EXAMPLE 7

A glass container was charged with 1 L of an aqueous solution containing a mixture of vinylbenzyltrimethyl ammonium salt (300 g) and acrylic acid (300 g). High-purity nitrogen was bubbled through the aqueous solution for 1 min to replace the dissolved oxygen. Subsequently, the aqueous solution was irradiated with γ-rays from cobalt 60 at a dose of 0.1 kGy/h for 1 h at room temperature to prepare a macromonomer. The degree of polymerization of the macromonomer was about 95. Glucose was added to the resulting macromonomer solution in an amount of 5% of the total quantity of the macromonomer and dissolved thoroughly to prepare a solution comprising a mixture of the macromonomer and glucose.

CLARINO (registered trademark), synthetic leather of Kuraray Co., Ltd., was immersed in an equal volume of the mixture solution for 10 min. Subsequently, the leather was recovered from the mixture solution, stripped off excess residual liquid and charged into an irradiation vessel. After deoxygenating the interior of the vessel, the leather was irradiated with γ-rays from cobalt 60 at a dose rate of 10 kGy/h for 2 h at room temperature, whereby the macromonomer was grafted onto the leather to produce a sample of the invention's adsorptive material. The sample was washed thoroughly with warm water to remove the unreacted macromonomer and the homopolymer of the macromonomer. After drying, the change in the weight of the adsorptive material was measured and the graft ratio was found to be 95 wt % of the impregnant macromonomer. The adsorptive material had no detectable deposit of a homopolymer of the macromonomer. Measurement of ion-exchange capacity showed that 4.0 mmol of anion-exchange groups had been introduced per gram of the adsorptive material.

What is claimed is:

1. An adsorptive material comprising a substrate having macromonomers, the macromonomers being bonded to the substrate and containing functional groups capable of adsorbing polar substances.

2. The adsorptive material according to claim 1 wherein the functional groups are hydrophilic groups and cationically dissociating groups and/or anionically dissociating groups.

3. The adsorptive material according to claim 1 wherein the degree of polymerization of the macromonomer is from about 10 to about 100.

4. The adsorptive material according to claim 1 wherein the macromonomer is bonded to the substrate by graft polymerization.

5. The adsorptive material according to claim 2 wherein the hydrophilic groups are at least one member selected from the group consisting of a hydroxyl group, a hydroxyalkyl group, an amino group and a pyrrolidonyl group.

6. The adsorptive material according to claim 2 wherein the cationically dissociating groups are at least one member selected from the group consisting of a carboxyl group, a sulfone group, a phosphate group, a sulfoethyl group, a phosphomethyl group and a carbomethyl group.

7. The adsorptive material according to claim 2 wherein the anionically dissociating groups are at least one member selected from the group consisting of a primary amino group, a secondary amino group, a tertiary amino group and a quaternary ammonium group.

8. The adsorptive material according to claim 1 wherein the substrate is in a fibrous form.

9. The adsorptive material according to claim 1 wherein the substrate is a cellulosic and/or polyolefinic substrate.

10. The adsorptive material according to claim 9 wherein the polyolefinic substrate is a halogenated polyolefin.

11. The adsorptive material according to claim 1 wherein the substrate is polyacrylonitrile.

12. The adsorptive material according to claim 1 wherein the substrate comprises animal hair.

13. The adsorptive material according to claim 1 wherein the substrate is a natural leather.

14. The adsorptive material according to claim 1 wherein the substrate is synthetic leather.

15. A process for producing an adsorptive material comprising the steps of applying to a substrate a mixture of a monosaccharide and macromonomers having functional groups capable of adsorbing polar substances and then grafting said macromonomers to said substrate.

16. The process according to claim 15 wherein the monosaccharide is aldohexose.

17. The process according to claim 16 wherein the monosaccharide is glucose.

18. The process according to claim 15 wherein grafting is done by radiation initiated graft polymerization.

19. The process according to claim 15 wherein the functional groups are hydrophilic groups and cationically dissociating groups and/or anionically dissociating groups.

20. The process according to claim 19 wherein the hydrophilic groups are at least one member selected from the group consisting of a hydroxyl group, a hydroxyalkyl group, an amino group and a pyrrolidonyl group.

21. The process according to claim 19 wherein the cationically dissociating groups are at least one member selected from the group consisting of a carboxyl group, a sulfone group, a phosphate group, a sulfoethyl group, a phosphomethyl group and a carbomethyl group.

22. The process according to claim 19 wherein the anionically dissociating groups are at least one member selected from the group consisting of a primary amino group, a secondary amino group, a tertiary amino group and a quaternary ammonium group.

23. The process according to claim 15 wherein the substrate is in a fibrous form.

24. The process according to claim 15 wherein the substrate is a cellulosic and/or polyolefinic substrate.

25. The process according to claim 24 wherein the polyolefinic substrate is a halogenated polyolefin.

26. The process according to claim 15 wherein the substrate is polyacrylonitrile.

27. The process according to claim 15 wherein the substrate comprises animal hairs.

28. The process according to claim 15 wherein the substrate is a natural leather.

29. The process according to claim 15 wherein the substrate is a synthetic leather.

* * * * *